US010463053B2

(12) United States Patent
Wubbolts et al.

(10) Patent No.: US 10,463,053 B2
(45) **Date of Patent: *Nov. 5, 2019**

(54) DISPERSION STRUCTURING AGENT

(71) Applicant: UPFIELD US INC., Englewood Cliffs, NJ (US)

(72) Inventors: Frank Emile Wubbolts, Utrecht (NL); Cynthia Akkermans, Amersfoort (NL); Tjerk De Vries, Eindhoven (NL); Ernst Jan Siewers, Alkmaar (NL); Daniela Oana Trambitas, Voorburg (NL); Rolf Sebastiaan Wilms, Rotterdam (NL)

(73) Assignee: UPFIELD US INC., Englewood Cliffs, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/051,170

(22) Filed: Jul. 31, 2018

(65) Prior Publication Data

US 2018/0338506 A1 Nov. 29, 2018

Related U.S. Application Data

(63) Continuation of application No. 13/127,662, filed as application No. PCT/NL2009/050665 on Nov. 4, 2009, now Pat. No. 10,064,418.

(30) Foreign Application Priority Data

Nov. 4, 2008 (EP) .................................... 08168271

(51) Int. Cl.
*A23D 7/02* (2006.01)
*A23D 7/01* (2006.01)
(Continued)

(52) U.S. Cl.
CPC ............... *A23D 7/02* (2013.01); *A23D 7/013* (2013.01); *A61K 8/046* (2013.01); *A61K 8/553* (2013.01);
(Continued)

(58) Field of Classification Search
None
See application file for complete search history.

(56) References Cited

U.S. PATENT DOCUMENTS

| | | |
|---|---|---|
| 3,892,880 A | 7/1975 | Grolitsch |
| 6,284,302 B1 | 9/2001 | Berger et al. |

(Continued)

FOREIGN PATENT DOCUMENTS

| | | |
|---|---|---|
| CA | 899710 A | 5/1972 |
| DE | 233484 A1 | 3/1986 |

(Continued)

OTHER PUBLICATIONS

International Search Report, PCT/ISA European Patent Office, dated Mar. 15, 2010.
(Continued)

*Primary Examiner* — Nikki H. Dees
*Assistant Examiner* — Amber M Cox
(74) *Attorney, Agent, or Firm* — Arent Fox LLP

(57) ABSTRACT

Disclosed is a novel method of making a structuring agent for edible dispersions such as margarines or spreads. Fat, or another structuring component, is subjected to a process involving mixing it with liquefied gas or supercritical gas, and expanding the mixture through an orifice. In the invention, water is added to the mixture prior to expansion, so as to provide a spray liquid in the form of a fat and water emulsion.

19 Claims, 2 Drawing Sheets

(51) Int. Cl.
*A61K 8/04* (2006.01)
*A61K 8/55* (2006.01)
*A61K 8/92* (2006.01)
*A61Q 19/00* (2006.01)
*C11B 15/00* (2006.01)

(52) U.S. Cl.
CPC .............. *A61K 8/922* (2013.01); *A61Q 19/00* (2013.01); *C11B 15/00* (2013.01)

(56) References Cited

U.S. PATENT DOCUMENTS

2004/0178529 A1   9/2004   Reverchon
2006/0280855 A1   12/2006  Van Den Berg et al.

FOREIGN PATENT DOCUMENTS

| EP | 1238589 A1 | 9/2002 |
| GB | 01924 A | 12/1913 |
| GB | 2031937 A | 4/1980 |
| WO | 2002100183 A2 | 12/2002 |
| WO | 2005014158 A1 | 2/2005 |

OTHER PUBLICATIONS

"Spray Drying" Spray Drying Definition in Quantachrome's particle characterization dictionary, http://www.quantachrome.co.uk/en/dictionary/spray-drying.asp (accessed Jul. 29, 2016), pp. 1.

DISPERSION STRUCTURING AGENT

CROSS-REFERENCE TO RELATED APPLICATIONS

This application is a continuation of U.S. patent application Ser. No. 13/127,662, filed on Sep. 20, 2011, which issued as U.S. Pat. No. 10,064,418, which is the National Stage Entry of PCT/NL2009/050665, filed on Nov. 4, 2009.

FIELD OF THE INVENTION

The invention pertains to the use as a dispersion structuring agent of a composition obtainable by a method comprising preparing a Spray Liquid comprising a structuring component, such as a fat, in a liquid state and gas in a liquefied or supercritical state distributed in the Spray Liquid, and expanding the mixture through an orifice. The invention also pertains to dispersion structuring agents so obtainable, edible oil-based dispersions comprising such a structuring agent, and to the use of a micronized fat powder to stabilize oil-containing dispersions.

BACKGROUND OF THE INVENTION

In general, structuring agents for dispersions are known. For a long time fatty compositions have existed that work as a dispersion structuring agent in edible water-in-oil emulsions, such as margarines and spreads. These edible dispersions typically have an oil phase that is a blend of liquid oil and fat that is solid at normal ambient temperature (20° C.). This solid fat, often also designated as hardstock, acts as a structuring agent, and its function is to stabilize the dispersion. To this end, traditionally, the dispersion is made by a process involving a temperature at which the oil phase, including the hardstock, is liquid, followed by cooling so as to form a fat crystal network that works to stabilize the dispersions and that lends some degree of firmness to the resulting product.

In WO 2005/014158 some drawbacks of the traditional hardstock, structuring agents are addressed. E.g., heating and cooling steps are involved that need to be applied to the whole weight of the dispersion, which requires a relatively high amount of energy. Further, the choice of suitable fats is relatively limited, as many fats will have inappropriate melting points to form a stabilizing crystal network at the appropriate temperature. In order to address these drawbacks, fine solid fat particles are employed as a structuring agent. These particles are preferably prepared by micronization. The disclosed process involves preparing a homogeneous mixture of structuring agent and liquefied gas or supercritical gas at a pressure of 5 to 40 MPa, and expanding the mixture through an orifice, under such conditions that a spray jet is applied in which the structuring agent is solidified and micronized.

As a further background on micronization of fats, U.S. Pat. No. 6,056,791 is referred to. This describes the preparation of micronized fat particles by dissolution of gas (carbon dioxide) in the fat under pressure, and decompressing the mixture in such a way that the temperature falls below the solidification point of the fat, so that micronized particles are formed.

Although the use of micronized fat as a structuring agent solves some of the aforementioned drawbacks of the traditional structuring agents, this does not mean that always as good a dispersion structuring is obtained as with the formation of a fatty crystal network through heating and subsequent cooling. Also, the powders formed by the micronization of fat are very fine, and may be difficult to handle during further processing. Moreover, despite this processing drawback, it is desired to use even finer particles, as the resulting higher surface area will contribute to the dispersion structuring capability of such particles.

Particle generation with supercritical $CO_2$ is an area of attention in many fields of technology. See e.g. E. Lack et al. *Particle Generation with Supercritical $CO_2$*, $1^{st}$ Vienna International Conference: Micro- and Nano-Technology (2005). Herein a variety of particles is illustrated, including fat encapsulated water.

SUMMARY OF THE INVENTION

In order to better address one or more of the aforementioned desires, the invention, in one aspect, is the use, as a dispersion structuring agent, of a composition obtainable by a method comprising preparing a Spray Liquid comprising a structuring component, such as a fat, in a liquid state and gas in a liquefied or supercritical state distributed in the Spray Liquid, subjecting the Spray Liquid to a first pressure $P_1$, expanding said mixture by spraying it through an orifice to an environment having a second pressure $P_2$, with $P_1 > P_2$, wherein water is added to the Spray Liquid prior to spraying so as to form an emulsion of fat and water as the Spray Liquid. In another aspect, the invention resides in a composition obtainable by this method. In a further aspect, the invention pertains to the use of said composition to stabilize a dispersion, preferably an edible dispersion comprising oil and structuring agent and one or more of an aqueous phase and/or a solid phase, such as a margarine, spread, or cosmetics. In yet another aspect, the invention provides a fat particle comprising an emulsifier having a hydrophilic moiety extending from the fat surface.

DETAILED DESCRIPTION OF THE INVENTION

In a broad sense, the invention is based on providing a Spray Liquid, i.e. the liquid that is to be expanded through an orifice, in which as compared to e.g. known fatty Spray Liquids, water is included.

Thus, the Spray Liquid comprises three main components, viz. a structuring component, such as a fat, in a liquid state, gas in a liquefied or supercritical state, and water.

The term Structuring Component is used to refer to fats, other lipids, and other hydrophobic substances such as waxes and sterols that are known, or can be envisaged, to have the ability to structure dispersions, particularly (edible) water-in-oil emulsions. As referred to in WO 2005/014158, a structuring agent functions to stabilize the dispersion. Representative classes, and examples, of such structuring components are given by Pernetti et al. in *Current opinion in Colloid and Interface Science* 12 (2007) 221-231. These include fats (triglycerides of fatty acids, i.e. triacyl glycerols or TAGs), or their dicacyl glycerol and mono acyl glycerol analogs (DAGs, MAGs, i.e. diglycerides resp. monoglycerides), fatty acids, fatty alcohols, waxes, wax esters, sorbitan alkylates, mixtures such as fatty acids with fatty alcohols, lecithin with sorbitan tristearate, phytosterols with oryzanol, and others.

The below description is written with reference to "fat" as a structuring component. This is done for the sake of legibility, and should be understood to be equally applicable to other embodiments of the structuring component.

It will be understood by the skilled person that these components need to be well distributed, and preferably are homogeneously distributed, over the spray liquid. This generally holds for emulsions, and it will be understood that therewith the distribution of the liquefied or supercritical gas over either or both of the lipid and aqueous phases is not particularly critical. Generally, the liquefied or supercritical gas will have an equilibrium distribution throughout the emulsion, the exact distribution depending on the water-lipid partition coefficient of the gas chosen and the particular combination of fat and water.

The emulsion can be a water-in-oil emulsion or an oil-in-water emulsion. To the extent that any system of liquid structuring component and water presented as the Spray Liquid might not be in a form generally recognized as an emulsion (e.g. if the ratio of the phases and the external circumstances are such that the Spray Liquid is in the form of a co-continuous system rather than an emulsion of one phase in the other) it is imperative that the system is homogenized.

The amount of water in the Spray Liquid can vary widely, e.g. from 5 to 95 wt. %, preferably from 25 to 80 wt/%, more preferably from 50 to 80 wt. % and most preferably 60-70 wt. %

It will be clear that in the lower ranges of these percentages (generally up to 50 wt. %), the emulsion will be a water-in-oil emulsion. The lower the water percentage herein, the more attention is to be paid to homogenizing the Spray Liquid, so as to ensure that the liquid that is expanded through the orifice actually contains both fat and water.

In the higher ranges (generally above 50 wt. %), the system will be an oil-in-water emulsion. Here too, the lower the fat percentage, the more stringent the homogenization that is needed to form an emulsion.

The person skilled in the art is well aware of techniques to produce emulsions of fat and water, both oil-in-water and water-in-oil emulsions. Typical equipment used is a homogenizer, such as an Ultra-Turrax.

The order of adding the aforementioned components to each other, so as to form the spray-liquid, is not critical. In cases of relatively large difference between the amounts of fat and water, it is preferred to first prepare the emulsion, preferably including a step of homogenizing the components, and then add the liquefied or supercritical gas.

In a preferred embodiment, in addition to the aforementioned main components, an emulsifier is added as a further component of the Spray Liquid. Whilst in general it is known to add emulsifiers to the fatty phase of a dispersion, the addition of an emulsifier to the Spray Liquid, prior to expansion, is believed to be associated with advantages particularly in connection with the fact that the Spray Liquid essentially comprises fat and water. Without wishing to be bound by theory, the present inventors believe that, as a result of the presence of fat and water in the Spray Liquid, the emulsifier will be located at the interface of fat and water before expansion. As a result, the expanded composition (i.e. the structuring agent) too will comprise fat and water, with the emulsifier positioned with its hydrophobic part within the fat, and its hydrophilic part within the water. When the fat component of the Spray Liquid is solidified, the water can be removed (e.g. if the solidified Spray Liquid is dried by evaporating the water), this results in a solid fat, preferably fat particles, provided with an emulsifier with a hydrophilic part extending from the fat surface. This "enhanced structuring fat" therewith has the desirable property of being a ready-to-use intermediate that can be added to an aqueous liquid and readily form an emulsion. This intermediate is suitable for widespread use, not only in margarines or other edible spreads. For use outside the nutritional field, it will be apparent to the skilled person that neither the fat nor the emulsifier is required to be edible. A preferred use is in cosmetics. Herein the fat and the emulsifier need to be cosmetically acceptable. Cosmetically acceptable fats and emulsifiers are known to the skilled person.

It will be understood that in a dispersion of fat in water, emulsifiers will generally be present in such a way as to have their hydrophobic part into the fatty phase, and the hydrophilic part into the aqueous phase. Different from this, and uniquely provided, the enhanced structuring agent of the invention refers to an isolated product, i.e. the term refers to the fat particle, provided with the emulsifier, before it is being put to use in an aqueous environment.

Provided that a fat is selected that is solid at ambient temperature (e.g. solid below at 25° C. or lower, preferably solid at 20° or lower), an advantage of the enhanced structuring fat, is that it comes in the form of a powder. This is convenient for handling, shipping, and processing. Fats having the appropriate solidification temperatures are commonly known to the skilled person.

In another embodiment, an intermediate product is prepared comprising the structuring agent of the invention, and preferably the enhanced structuring agent of the invention, pre-dispersed in oil. Particularly if this is done at low shear, a pourable composition will result. This embodiment yields advantages in the sense that it well fits within the regular supply chain for oils, i.e. the structuring agent can be handled, shipped, and processed just as the oil is. This is by virtue of the fact that the structuring agent of the invention can be mixed with oil so as to form a mixture is flowable and/or pumpable. Also, it remains stable and maintains its structuring properties for a long time. The fat (or fat powder) content in the fat-oil mixture ranges from 2.5-20% by weight, preferably 5-15% by weight.

The use of the expanded composition as a dispersion structuring agent, will involve mixing the structuring agent with oil, typically an edible oil as used in a margarine or spread, or with a pre-existing mixture of oil and water.

When the structuring agent is mixed with the oil, or with the mixture of oil and water, and further processed into a dispersion such as a margarine or spread, generally a rearrangement of the aqueous and lipid components will take place. Herein, the micronized fat of the expanded mixture will serve as a structuring agent. The water, including the water present in the structuring agent, will form the aqueous phase of the resulting dispersion. With the emulsifier already present in the fat phase of the structuring agent, the surface of the fat provided through the expansion of the Spray Liquid, is already loaded with a well-oriented emulsifier, and will therefore be capable of a favourable interaction with the aqueous phase.

This advantage, through which improved micronized fat is generated in that it is provided with hydrophilic surface properties, can already be attained with a low water percentage (with appropriate homogenization even below the 5 wt. %, and particularly in the case of 1-15 wt. % water and preferably 5-25 wt. % of water). Of course, the same advantage will hold for higher water-percentages.

The emulsifier will be generally present in an amount customary in the art, preferably 0.1% to 5% by weight.

Spray Liquids having relatively high water-percentages, are preferred in view of a further advantage. Since water has a higher density than fat, the addition of water is a powerful tool to prepare a micronized fatty composition of heavier weight than the corresponding micronized fat itself. This enables easier handling of the structuring agent during further processing. It will be apparent to the skilled person that the extent to which the advantage of an increased weight is obtained, scales with the amount of water incorporated in the Spray Liquid.

As a further advantage to the invention, it will be apparent that a wider choice of materials is possible than in the case of building a stabilising network of particles as with traditional hardstock (see also Pernetti et al. (2007), referred to above).

Preferably, the structuring component is fat (or mixture of fats), and more preferably it is edible fat. Edible fats consist predominantly of triglycerides. Typically such edible fats suitable as a component of the structuring agent of the invention are mixtures of triglycerides, some of which have a melting point higher than room or ambient temperature and therefore contain solids in the form of crystals. Generally, fats with a high content of HUH triglycerides show good structuring properties. H denotes a C16-C24 saturated fatty acid residue, such as palmitic acid (C16) or stearic acid (C18) and U denotes an unsaturated C18 fatty acid residue, such as oleic acid (C18:1) or linoleic acid (C18:2). Examples of suitable edible fat structuring agents (hardstock fats) are palm oil partially hydrogenated to a melting point of 44 C or an interesterified mixture of palm oil and a lauric fat.

The fat phase in the structuring agent of the invention can further comprise customary ingredients such as coloring agents and flavors, and emulsifiers, such as monoglycerides and lecithin. As explained above, the addition of an emulsifier in the water-containing structuring agent provides a particular advantage of the present invention. Suitable emulsifiers include lecithin, hydroxylated lecithin and mono-, di- or polyglycerides of fatty acids, such as monostearin and monopalmitin, acetylated monoglycerides, glycerol esters, polyglycerol esters, propylene glycol esters, polyoxyethylene sorbitan esters, sorbitan esters, sodium citrate, sodium lactate, sodium stearoyl-2-lactylate, stearyl-2-lactylic acid, and mixtures thereof. Lecithin is a preferred emulsifier.

The structuring agent of the invention is obtainable using a micronization process. In the micronization process the structuring agent is prepared by providing the aforementioned emulsion, preferably a homogeneous mixture, of fat, water, and liquefied gas or supercritical gas at a pressure of 5-40 MPa and expanding the mixture through an orifice, preferably under such conditions that a spray jet is applied in which the structuring agent is at least partially solidified. The liquefied gas or supercritical gas may be any gas that may be used in the preparation of food products, for example carbon dioxide, propane, ethane, xenon or other noble gases. Mixtures of gases can be used. Carbon dioxide and propane are preferred, with carbon dioxide being the most preferred. Advantages of carbon dioxide are that it has a mild (31° C.) critical temperature, it is non-flammable, nontoxic, environmentally friendly and it may be obtained from existing industrial processes without further contribution to the greenhouse effect. It is fairly miscible with oil and is readily recovered owing to its high volatility at ambient conditions. Finally liquid $CO_2$ is the second least expensive solvent after water.

The temperature of the mixture of structuring agent and liquefied gas or supercritical gas is preferably such that a homogeneous mixture is formed. Advantageously, the temperature of the mixture of structuring agent and liquefied gas or supercritical gas is below the slip melting point of the structuring agent at atmospheric pressure and above the temperature at which phase separation of the mixture occurs. Under such conditions the smallest micronized particles may be obtained.

The pressure and temperature of the Spray Liquid (i.e. the mixture of fat, water, and liquefied or supercritical gas) is preferably such that a large amount of the gas may be dissolved in the emulsion of fat and water. The amount dissolved will be determined by the phase diagram of the mixture of structuring agent and liquefied or supercritical gas. At higher pressures as well as at lower temperatures more gas will dissolve in the Spray Liquid.

Preferably the temperature and pressure are chosen such that 10 wt. % or more, more preferably 20 wt. % or more or most preferably 30 wt. % or more of gas is dissolved in the Spray Liquid. The Spray Liquid may contain additional substances, such as for instance oil. The addition of oil may reduce sintering of the micronized particles of the structuring agent.

The Spray Liquid is depressurized over a small orifice or nozzle, to break up the liquid into small droplets. The break-up of the liquid into droplets can be assisted e.g. by internals inside the nozzle before the orifice to generate a whirl, or by passing a gas at a high flow rate near the orifice.

The mixture is depressurized into a volume where the pressure is higher than, equal to or lower than atmospheric pressure.

In the foregoing process steps the Spray Liquid is subjected to a first pressure, $P_1$, and expanded (depressurized) at a second pressure, $P_2$, with $P_1$ greater than $P_2$. Preferably, $P_1$ is at least a factor 10 greater than $P_2$, and more preferably this factor is about 50-500. Most preferably, $P_1$ is a factor 200-400 greater than $P_2$, e.g. 300. As mentioned above, $P_1$ preferably is 5-40 MPa. $P_2$ most preferably is ambient pressure, i.e. generally the local atmospheric pressure.

Sintering, agglomeration and ripening of micronized particles of the structuring agent will lead to a reduced performance of the particles for structuring the dispersion. To avoid sintering, agglomeration and/or ripening of the micronized particles, preferably a gas jet is applied in addition to the flow of the spray jet. The additional gas jet is most effective when the gas jet is positioned such that recirculation of material expanded through the orifice is reduced or avoided. Especially advantageous is a position wherein the gas from the gas jet flows essentially tangentially to the flow direction of the spray jet. Most advantageously the gas inlet for the gas jet is positioned behind the exit of the nozzle, see FIG. 2. FIG. 2 shows that the additional gas inlet (1) behind the exit of the nozzle (2) creates a gas flow (3) tangentially to the flow of the spray jet (4).

To further avoid agglomeration and ripening, the spray jet is preferably sprayed into a collection chamber, and a flow of gas having a temperature lower than the slip melting point of the fat is fed into the collection chamber.

The expanded Spray Liquid according to the invention can be used as a structuring agent in a dispersion. A dispersion is herein defined as a system in which two or more phases that are insoluble or only slightly soluble are distributed in one another. The dispersion may be an emulsion, a suspension or foam or any combination thereof, it may be oil continuous, water continuous or bi-continuous. Preferably the dispersion is oil continuous, more preferably an oil continuous emulsion or oil continuous suspension. Where a solid phase is present in the dispersion according to the invention, it is preferably a solid phase of dry particulate matter. Where an aqueous phase is present in the dispersion according to the invention, it is preferably a dispersed aqueous phase.

According to the invention, the dispersion can be formed by mixing oil, the structuring agent of the invention, and the other phase or phases of the dispersion, such as for example an aqueous phase, a solid phase and/or a gas phase.

Preferably the edible dispersion according to the invention is a water and oil containing emulsion, optionally including a solid phase. The emulsions are preferably oil continuous. Examples of suitable emulsions are table spreads, dressings, soups, sauces, shortenings, cooking oils, frying oils, whipping creams and mayonnaises.

In this case a particularly advantageous embodiment of the invention is to mix the water-containing structuring agent (i.e. the product obtainable by the expansion of the Spray Liquid) with oil, so as to have the water from the structuring agent as the sole source of water in the emulsion. This is particularly suitable with structuring agent of a relatively high water-content (e.g. 50-80 wt. %). In that case two advantages are synergistically combined: the fact that water is contained in the structuring agent allows the direct combination with the oil, which leads to a simple process of manufacturing the emulsion, i.e. the margarine or the like, by basically combining only two streams of ingredient. And, moreover, the improved handling of the heavier, water-containing structuring agent also contributes to allowing a simpler production process.

Suitable oils are, e.g., customary margarine oils such as corn oil, cottonseed oil, sunflower oil, palm oil, rapeseed oil, or mixtures thereof.

A further preferred edible dispersion according to the invention is a dispersion of a solid matter, preferably a dry particulate matter, dispersed in a continuous phase of oil and structuring agent. Preferred material for the dry particulate matter is one or more of flour, starch, salt, herbs (e. g. dried herbs), spices and mixtures thereof. Preferably in such dispersions, the amount of solid matter is 30-75 wt. %, more preferably 40-65 wt. % based on total weight of the dispersion.

The amount of structuring agent should be such that a suitably stable dispersion is obtained. When the structuring agent is micronized fat, the amount is preferably 1-20 wt. %, more preferably 4-12 wt. % based on total weight of the dispersion.

The mixing of the ingredients may be done in any order, i.e. the ingredients/phases may all be mixed in one mixing step or alternatively the mixing may be executed in more than one step. For instance an oil phase with the structuring agent may be mixed and a water phase may be prepared separately and later mixed with the oil phase.

A stable solid dispersion is herein defined as dispersion that shows a phase separation of less than 5% after storage for 10 weeks at 21° C., determined by examining the surface of the product and measuring the amount of water exudated. A stable pourable dispersion is herein defined as dispersion that shows less an oil exudation of less than 2% after storage for two weeks at 21° C., determined by measuring the height of the free oil layer that appears on top of the product. This free oil layer is considered a product defect.

EXAMPLES

Method to Determine Pourability

Figure 1:
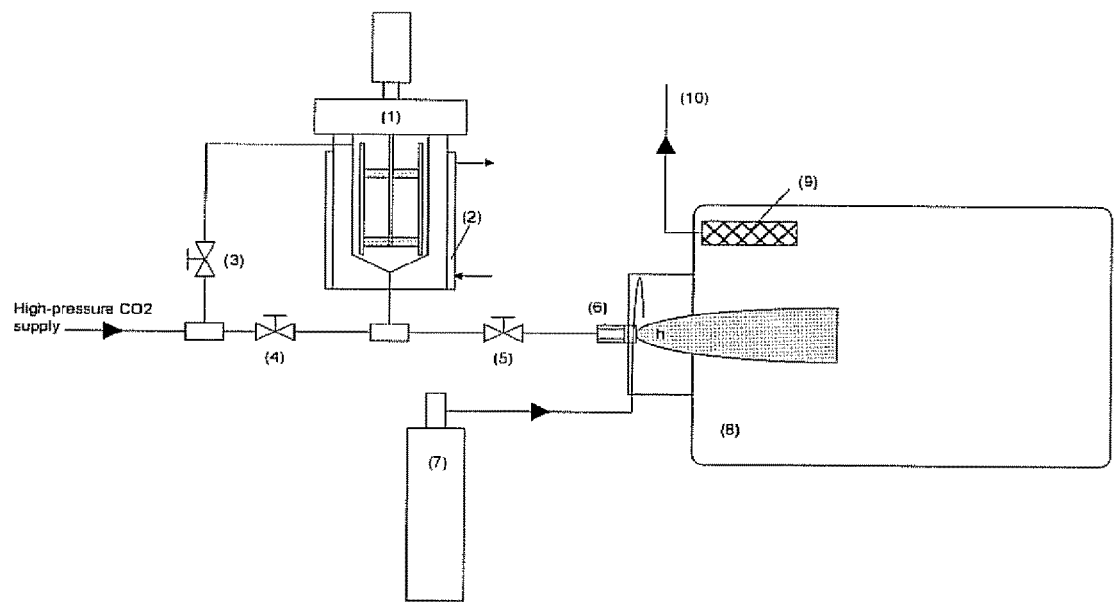
FIG. 1 is a schematic view of the micronisation apparatus used in the examples. The equipment consists of a 1-liter autoclave (1) equipped with a mechanical stirrer (anchor-type impeller), and a jacket for heating (2). The inner diameter of the autoclave is 50 mm. The autoclave has connections at the top and at the bottom. The bottom connection of the vessel is used to pressurize the system with carbon dioxide by opening valve (4), or to lead the spray liquid from the autoclave to the nozzle by opening valve (5). Before expelling the mixture from the vessel, valve (4) is closed and the $CO_2$ supply is connected to the top of the autoclave by opening valve (3) to maintain the pressure inside the autoclave during spraying. Instead of $CO_2$ other gases (e.g. $N_2$, He, Ar) can be used to maintain the pressure. The orifice and an insert of the nozzle (6) can be changed independently. The nozzle is mounted on top of a tube of 30 cm diameter and 20 cm length. The tube is mounted on an oil-drum (8) of 250 liters with a removable lid. The product that is formed during the expansion collects inside the drum. All gas that enters the drum leaves through the gas exit (10). A separator (9) in the exit retains the product. Additional cooling can be added e.g. $CO_2$ expanding from a cylinder (7) through an inlet into the spray chamber.
Figure 2:
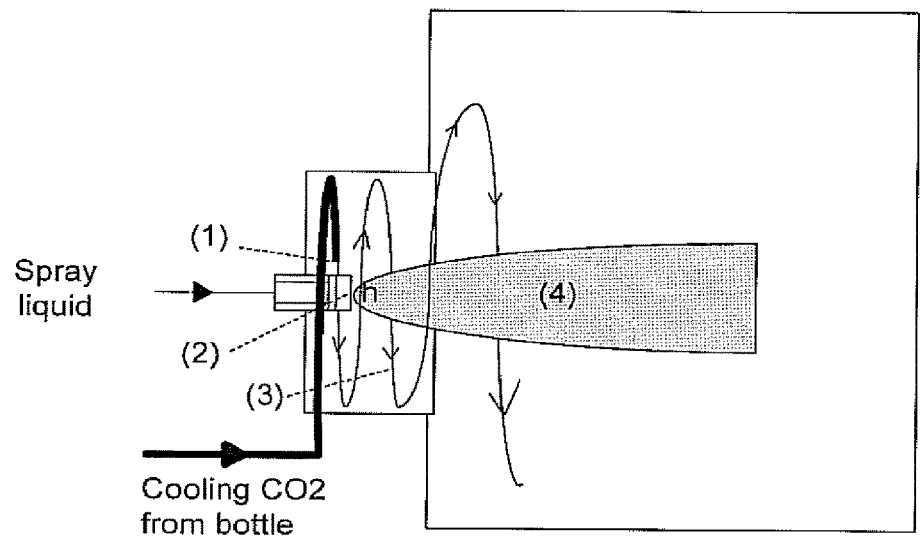
FIG. 2 is a schematic view of the nozzle configuration with gas inlet for tangential gas-flow.
Figure 3:
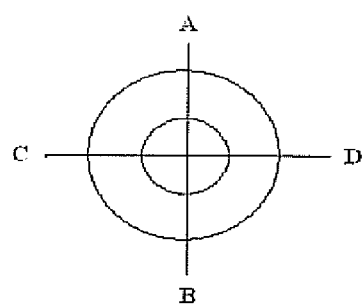
FIG. 3 illustrates the measurement points (A, B, C, D) used to measure flow on a board with concentric circles, as used in the example on determining pourability. These concentric circles are used to indicate the distance the fluid has travelled during a certain period of time

Pourability for pourable compositions according to the invention is measured using an instrument based on USDA consistometer or Adam's consitometer. It consists of a 10 ml plastic cylinder with both ends open and a board with concentric circles. These concentric circles are used to indicate the distance the fluid has travelled during a certain period of time. The pourability of the samples is assessed at refrigerator temperature in order to analyze if they are pourable at fridge temperature. When the sample has a temperature of 4° C., the plastic tube is placed at the central circle of the concentric circles and it is filled with the sample after it has been shaken by hand ten times up and down. When the tube is removed, the sample starts to flow and spreads over the board. The path length of the flow is measured after 40 seconds at four different points of the concentric circles (A, B, C, and D) as it is shown in FIG. 3. The weight of the board is measured before and after the test is carried out so that the mass of sample on the board can be calculated and the pourability of the sample can be expressed as cm/g per 40 seconds. The pourability is assessed twice, after approximately 5 and 10 days of the production of the sample.

Method to Determine Hardness

The instrument used for the hardness analysis is the gravity-penetrometer PNR 10. A metallic cone with a 90° angle was employed as the test body. The cone is precisely lowered to the surface of the material under test, and then sinks into the matter by its own weight during defined test duration of 5 seconds. This penetration allows a rating of the plasticity or consistency. Hardness of the samples was analyzed at refrigerator temperature and after 6 and 10 days of their production. Hardness can be expressed as penetration depth (mm) or yield value.

Method to Determine Density of the Structuring Powder

The density was determined by filling a 100 ml measuring cylinder with powder and weighing the amount of powder.

After filling the cylinder is dropped three times from 2 cm height before the volume is determined.

Method to Determine Oil Exudation for Pourable Samples

In order to measure oil exudation, the product is filled into a scaled plastic cylinder of 50 ml. The filled cylinder is stored in a cabinet at constant temperature (21° C.). After two weeks the height of the exuded oil layer is measured and oil exudation is expressed as the height of the exuded oil layer divided by the original filling height and expressed in %. Shaking of the cylinders should be avoided.

Method to Determine Water Exudation for Solid Samples

Samples were stored in a 50 ml plastic container at 21° C. for up to 10 weeks. After storage the amount of water exudation was determined by visual examination of the product surface and by measuring the weight of the exuded water. Water exudation is expressed as the weight of exuded water divided by the total weight of the sample and expressed in %.

Preparation of Structuring Agent (SA)

A spray liquid was prepared from melted fat and a solution of lecithin in hot water by homogenization with a Turrax. The spray liquid was loaded into a heated autoclave of 1 liter as in FIG. (1), keeping a headspace to allow the liquid level to rise during the addition of $CO_2$. While stirring, the autoclave was pressurized to 300 bars by adding carbon dioxide. After equilibration the mixture was withdrawn through the bottom connection of the autoclave and sprayed into a receptor vessel at ambient pressure. During spraying the pressure in the autoclave was maintained by adding carbon dioxide through a connection in the top of the autoclave. Cold gas in the form of carbon dioxide expanded from a storage cylinder was blown into the receptor vessel as in FIG. (2) to provide additional cooling. The temperature of the gas that leaves the spray vessel is typically maintained at 0° C. by adjusting the flow of cooling gas. The structuring agent (SA) was recovered from the receptor vessel and stored in a refrigerator for later use.

Spray Liquid Compositions:

|   | Water (g) | Fat (g) | Lecithin (g) |
|---|---|---|---|
| A | 795 | 200 | 5 |
| B | 595 | 400 | 5 |
| C | 395 | 600 | 5 |
| D | 195 | 800 | 5 |
| E | 0 | 1000 | 0 |

Structuring Agent Properties:

|   | Water | Powder density |
|---|---|---|
| A | 80% wt | 0.34 g/ml |
| B | 55% wt | 0.19 g/ml |
| C | 32% wt | 0.16 g/ml |
| D | 14% wt | 0.16 g/ml |
| E | 0% wt | 0.10 g/ml |

Pourable Margarine

To test the structuring ability of the structuring agents (of which the preparation is described in example 1), a pourable margarine product was made of each structuring agent. The pourable margarines consisted of 75.5 wt % sunflower oil, 18.8 wt % water, 3.5 wt % fat (RP 70), 0.5 wt % lecithin, 0.5% glyceryl monostearate (GMS) and 1.2 wt % salt (NaCl). RP 70 and a part of the water were present as the structuring agent. Some samples were also produced using less fat (2.0%).

Lecithin and GMS were melted in the sunflower oil and salt is dissolved in water. When both solutions are cooled (~4° C.), they were emulsified using an Ultra Turrax (high speed). The structuring agent was added to the emulsion using a magnetic stirrer. A vacuum pump was used to remove the air bubbles from the samples. The obtained dispersion was kept at a temperature of 4° C. until analysis. The pourable margarines were analyzed for their stability (oil exudation) and pourability.

Pourable Margarine Composition:

|   | Weight | | |
|---|---|---|---|
|   | SA | SF-Oil | Water |
| Pourable A-1 | A | 75.5% wt | 18.8% wt |
| Pourable B-1 | B | 75.5% wt | 18.8% wt |
| Pourable C-1 | C | 75.5% wt | 18.8% wt |
| Pourable D-1 | D | 75.5% wt | 18.8% wt |
| Pourable E-1 | E | 75.5% wt | 18.8% wt |
| Pourable A-2 | A | 77.0% wt | 18.8% wt |
| Pourable B-2 | B | 77.0% wt | 18.8% wt |
| Pourable C-2 | C | 77.0% wt | 18.8% wt |
| Pourable D-2 | D | 77.0% wt | 18.8% wt |
| Pourable E-2 | E | 77.0% wt | 18.8% wt |

Pourable Margarine Properties:

|   | Stability | Pourability day 5 | Pourability day 10 |
|---|---|---|---|
| Pourable A-1 | ~0% vol | 0.32 cm/g | 0.33 cm/g |
| Pourable B-1 | 0.5% vol | 0.33 cm/g | 0.34 cm/g |
| Pourable C-1 | ~0% vol | 0.32 cm/g | 0.33 cm/g |
| Pourable D-1 | ~0% vol | 0.34 cm/g | 0.34 cm/g |
| Pourable E-1 | ~0% vol | 0.34 cm/g | 0.35 cm/g |
| Pourable A-2 | 9.3% vol | 0.43 cm/g | 0.40 cm/g |
| Pourable B-2 | 10.8% vol | 0.41 cm/g | 0.41 cm/g |
| Pourable C-2 | 16.7% vol | 0.45 cm/g | 0.42 cm/g |
| Pourable D-2 | 21.6% vol | 0.43 cm/g | 0.43 cm/g |
| Pourable E-2 | 22.1% vol | 0.45 cm/g | 0.43 cm/g |

Spreads

To test the structuring ability of the structuring agents (of which the preparation is described in example 1), a spread product was made of each structuring agent. The spreads consisted of 49.75 (solid A) or 60 wt % sunflower oil, 29 or 39.75 (solid A) wt % water, 10 wt % fat (RP 70), 0.5 wt % lecithin and 0.5 wt % protein (whey protein isolate). RP 70 and a part of the water were present as the structuring agent. For sample Solid A, RP 70 and all the water were present as the structuring agent.

Lecithin was melted in the sunflower oil and the mixture was cooled (~4° C.). The structuring agent was added to the oil mixture using an Ultra Turrax. Whey protein was dissolved in water and the aqueous phase was cooled (~4° C.). The aqueous phase is admixed to the fat phase using an Ultra Turrax. While the aqueous phase was being added, a cool water bath was used to keep the mixture cold. The spreads were kept at a temperature of 4° C. The solid margarines were analyzed for their hardness and stability (water exudation).

Spreads Composition:

|   | Weight | | |
|---|---|---|---|
|   | SA | SF-Oil | Water |
| Solid A | A | 49.75% wt | 39.75% wt |
| Solid B | B | 60.0% wt | 29.0% wt |
| Solid C | C | 60.0% wt | 29.0% wt |

-continued

|  | Weight | | |
| --- | --- | --- | --- |
|  | SA | SF-Oil | Water |
| Solid D | D | 60.0% wt | 29.0% wt |
| Solid E | E | 60.0% wt | 29.0% wt |

Spreads Properties:

|  | Penetration depth/ Yield value Day 5 | Day 10 | Stability |
| --- | --- | --- | --- |
| Solid A | 4.01 mm/149 | 3.66 mm/149 | 0.54% wt |
| Solid B | 10.17 mm/29 | 10.26 mm/29 | 0.03% wt |
| Solid C | 11.71 mm/23 | 11.80 mm/23 | 0.10% wt |
| Solid D | 12.27 mm/23 | 11.83 mm/23 | 0.02% wt |
| Solid E | 10.42 mm/28 | 11.63 mm/23 | 0.33% wt |

The invention claimed is:

1. A method for making a composition suitable for use as a dispersion structuring agent, the method comprising:
   a) preparing a spray liquid comprising:
      a structuring component comprising a fat in a liquid state,
      a gas in a liquefied or supercritical state distributed in the spray liquid, and
      an emulsifier;
   b) subjecting the spray liquid to a first pressure $P_1$;
   c) adding water to the spray liquid subjected to the first pressure $P_1$ prior to spraying to form a spray liquid mixture comprising an oil-in-water emulsion of the structuring component and water, wherein the water in the spray liquid mixture comprises from 50 to 80 wt. %; and
   d) expanding the spray liquid mixture by spraying it through an orifice to an environment having a second pressure $P_2$, with $P_1 > P_2$;
   wherein the dispersion structuring agent comprises fat and water.

2. The method of claim 1, wherein the composition suitable for use as a dispersion structuring agent has a powder density of from 0.16 g/ml to 0.34 g/ml.

3. The method of claim 1, wherein the water in the spray liquid mixture comprises 60 to 70 wt. %.

4. The method of claim 1, wherein $P_1$ is 5-40 MPa and $P_2$ is ambient pressure.

5. The method of claim 1, wherein in the expanding step, the spraying is conducted by means of a spray-jet wherein the spray liquid is at least partially solidified.

6. The method of claim 1, wherein the gas is supercritical carbon dioxide.

7. The method of claim 1, wherein the water in the composition is the sole source of water in the emulsion.

8. The method of claim 1, wherein in the expanding step d) the spray liquid is solidified by spraying the spray liquid mixture through the orifice, and the method further comprises removing water from the structuring agent when the structuring component of the spray liquid is solidified to obtain a solid fat or solid fat particles.

9. The method of claim 1, wherein the dispersion is a margarine.

10. A mixture comprising (a) an oil and (b) the dispersion structuring agent of claim 1 comprising fat and water.

11. The mixture of claim 10, wherein the fat content in the mixture ranges from 2.5-20% by weight.

12. The mixture of claim 10, wherein the mixture is dispersed with water.

13. The mixture of claim 10, wherein the fat content in the mixture ranges from 5-15% by weight.

14. A method for making a stabilized oil-containing dispersion, comprising the following steps:
   a) making a structuring agent, comprising the steps of:
      i) preparing a spray liquid comprising: a structuring component in a liquid state, a gas in a liquefied or supercritical state distributed in the spray liquid, and an emulsifier, the structuring component being a fat;
      ii) subjecting the spray liquid to a first pressure $P_1$;
      iii) adding water to the spray liquid subjected to the first pressure $P_1$ prior to spraying to form an oil-in-water emulsion of the structuring component and water as a spray liquid mixture, wherein the water in the spray liquid mixture comprises from 50 to 80 wt. %; and
      iv) expanding the spray liquid mixture by spraying it through an orifice to an environment having a second pressure $P_2$, with $P_1 > P_2$;
   b) mixing oil and the structuring agent to prepare an oil-structuring agent mixture; and
   c) mixing the oil-structuring agent mixture with an aqueous phase to form a dispersion, wherein the dispersion comprises fat and water.

15. The method of claim 14, wherein the structuring agent has a powder density of from 0.16 g/ml to 0.34 g/ml.

16. The method of claim 14, wherein $P_1$ is 5-40 MPa and $P_2$ is ambient pressure.

17. The method of claim 14, wherein in the expanding step, the spraying is conducted by means of a spray-jet wherein the spray liquid is at least partially solidified.

18. The method of claim 14, wherein the water in the spray liquid mixture comprises from 60 to 70 wt. %.

19. The method of claim 14, wherein the gas is supercritical carbon dioxide.

* * * * *